United States Patent [19]

Suzuki et al.

[11] Patent Number: 5,939,304
[45] Date of Patent: Aug. 17, 1999

[54] METHOD FOR SYNTHESIS OF ANHYDROTHROMBIN

[75] Inventors: Toyoaki Suzuki, Tokyo; Kazuya Hosokawa, Kawasaki; Masanori Nagata, Tokyo, all of Japan

[73] Assignee: Fujimori Kogyo Co., Ltd., Tokyo, Japan

[21] Appl. No.: 09/088,244

[22] Filed: Jun. 1, 1998

[30]  Foreign Application Priority Data

Jun. 5, 1997 [JP] Japan ..................................... 9-148116
Apr. 30, 1998 [JP] Japan ................................. 10-120859

[51] Int. Cl.$^6$ ................................................. A61K 38/48
[52] U.S. Cl. ............................................................ 435/214
[58] Field of Search ............................................. 435/214

[56]  References Cited

PUBLICATIONS

"Anhydrotrypsin: New Features in Ligand Interactions Revealed by Affinity Chromatography and Thionine Replacement" by Yokosawa and Ishii; J. Biochem, 81, pp. 647–656 (1977).
"Anhydrotrypsin and Trypsin: Subtle Difference in the Active–site Conformations Detected by Chemical Modification and CD Spectroscopy" by Yokosawa and Ishii; J. Biochem, 81, pp. 657–663 (1977).
"The Preparation of Anhydro–Trypsin and Its Reactivity With Naturally Occurring Proteinase Inhibitors" by Ako, Foster and Ryan, Biochemical and Biophysical Research Communications, vol. 47, No. 6, 1972, pp. 1402–1407.

"The Purification by Affinity Chromatography of a Proteinase Inhibitor Binding Species of Anhydro–Chymotrypsin" by Ako, Ryan and Foster; Biochemical and Biophysical Research Communications, vol. 46, No. 4, 1972, pp. 1638–1645.
"Preparation and Characterization of Anhydrothrombin" by Ashton and Scheraga; Biochemistry 1995, 34, pp. 6454–6463.
"Preparation of Anhydro–thrombin and Its Interacton with Plasma Antithrombin III" by Tomono and Sawada; ACTA Haematologica Japonica, vol. 49, No. 4, pp. 969–979, 1986.
Japanese Patent Application No. JP–B–59–7694 with English Abstract.

Primary Examiner—Jean C. Witz
Attorney, Agent, or Firm—Woodbridge & Associates

[57]  ABSTRACT

A method for a synthesis of anhydrothrombin is provided which features a short process, an easy procedure, and high yields.

The method comprises (A) a step of causing an active serine residue site of thrombin to react with an inhibitor,
(B) a step of performing an alkali treatment at a pH of not less than 11, and
(C) a step of performing an operation of recovery, and carries out these steps sequentially in the order mentioned, and is characterized by causing at least the step of performing the operation of recovery to proceed in the presence of at least one compound selected from the group consisting of polyhydric alcohols and saccharides, and a salt or an amphoteric electrolyte.

5 Claims, 1 Drawing Sheet

| Conventional process | | Process of this invention |
|---|---|---|
| Process A | Process B | |
| α-Thrombin/50 mM Tris-HCl 0.1 M NaCl<br>↓ Kept hot for 5 min<br>Addition of PMSF<br>↓ Kept at 20°C for two hrs<br>Adjusted to pH 9 with 0.1 N NaOH<br>↓<br>Dialyzed for 24 hrs<br>↓<br>Concentrated with PM-10 membrane<br>↓<br>Adjusted to pH 7.5<br>↓<br>Subjected to affinity chromatography with benzamidine cepharose 4B<br>↓<br>Dialyzed for 24 hrs | α-Thrombin/50 mM phosphoric acid buffer 0.1 M NaCl 0.1 PEG<br>↓<br>PMSF added<br>↓<br>Buffer solutions exchanged with a column of Sephadex<br>↓<br>Concentrated with a YM-10 membrane<br>↓<br>6 N Gdn-HCl/6N NaOH added<br>↓ stirred for 10 min<br>0.4 M phosphoric acid buffer pH 6 added<br>↓<br>0.75 M NaCl 0.1% PEG added dropwise to phosphoric acid buffer solution<br>↓<br>Concentrated with a YM-10 membrane<br>↓ Kept for 20 hrs<br>PMSF added again<br>↓<br>Exchange of buffer solutions in a column of Sephadex<br>↓<br>Subjected to affinity chromatography with benzamidine cepharose<br>↓ Analysis of fraction of solution for protein content<br>Dialyzed to effect removal of benzamidine | Thrombin/5mM phosphoric acid buffer 0.1 M NaCl<br>↓<br>PMSF added<br>↓<br>Subjected to gel filtration<br>↓<br>1 N NaOH added and left reacting at 0°C for 12 min<br>↓<br>NaCl and glycerin added, adjusted to pH 8 with 1 M Tris-HCl of pH 7, and left standing at 4°C for 12 hrs<br>↓<br>Dialyzed for 12 hrs<br>↓<br>Concentrated with a YM-10 membrane<br>↓<br>Subjected to affinity chromatography in a column of benzamidine cepharose<br>↓ Analysis of fraction of solution for protein content<br>Dialyzed to effect removal of benzamidine |
| Total: About 60 hrs | Total: About 72 hrs | Total: About 43 hrs |

Fig. 1

| Conventional process | | Process of this invention |
|---|---|---|
| Process A | Process B | |
| α-Thrombin/50 mM Tris-HCl 0.1 M NaCl<br>↓ Kept hot for 5 min<br>Addition of PMSF<br>↓ Kept at 20°C for two hrs<br>Adjusted to pH 9 with 0.1 N NaOH<br>↓<br>Dialyzed for 24 hrs<br>↓<br>Concentrated with PM-10 membrane<br>↓<br>Adjusted to pH 7.5<br>↓<br>Subjected to affinity chromatography with benzamidine cepharose 4B<br>↓<br>Dialyzed for 24 hrs | α-Thrombin/50 mM phosphoric acid buffer 0.1 M NaCl 0.1 PEG<br>↓<br>PMSF added<br>↓<br>Buffer solutions exchanged with a column of Sephadex<br>↓<br>Concentrated with a YM-10 membrane<br>↓<br>6 N Gdn-HCl/6N NaOH added<br>↓ Stirred for 10 min<br>0.4 M phosphoric acid buffer pH 6 added<br>↓<br>0.75 M NaCl 0.1% PEG added dropwise to phosphoric acid buffer solution<br>↓<br>Concentrated with a YM-10 membrane<br>↓ Kept for 20 hrs<br>PMSF added again<br>↓<br>Exchange of buffer solutions in a column of Sephadex<br>↓<br>Subjected to affinity chromatography with benzamidine cepharose<br>↓ Analysis of fraction of solution for protein content<br>Dialyzed to effect removal of benzamidine | Thrombin/5mM phosphoric acid buffer 0.1 M NaCl<br>↓<br>PMSF added<br>↓<br>Subjected to gel filtration<br>↓<br>1 N NaOH added and left reacting at 0°C for 12 min<br>↓<br>NaCl and glycerin added, adjusted to pH 8 with 1 M Tris-HCl of pH 7, and left standing at 4°C for 12 hrs<br>↓<br>Dialyzed for 12 hrs<br>↓<br>Concentrated with a YM-10 membrane<br>↓<br>Subjected to affinity chromatography in a column of benzamidine cepharose<br>↓ Analysis of fraction of solution for protein content<br>Dialyzed to effect removal of benzamidine |
| Total: About 60 hrs | Total: About 72 hrs | Total: About 43 hrs |

METHOD FOR SYNTHESIS OF ANHYDROTHROMBIN

BACKGROUND OF THE INVENTION

1. Field of the Invention

This invention relates to a method for a synthesis of anhydrothrombin. More particularly, this invention relates to a method for a highly efficient and convenient synthesis of anhydrothrombin having a specific ability as a ligand to be utilized for the technique of affinity chromatography which is effectively adopted for separating and refining antithrombin III, blood coagulation factors VIII and XIII, etc.

2. Description of Related Art

The antithrombin III, one species of the glycoprotein which belongs to an $\alpha_2$-globulin in blood plasma, discharges an important role of inhibiting the reaction of blood coagulation or adjusting a reaction of coagulation in the blood vessel by reacting with thrombin or an activating factor and forming a corresponding complex.

As respects the method for separating and purifying the antithrombin of this quality, the technique of affinity chromatography which effects the separation by virtue of the specific affinity for a heparin (ligand) is at an advantage in (1) simplifying the operation of purification, (2) allowing satisfactory separation of extraneous substances, and (3) enjoying a satisfactory activity recovery ratio.

When this technique is used for isolating the antithrombin III from a side fraction obtained by the cold ethanol technique which is widely practiced on a commercial scale, however, the product occurs in very low yields. When this substance is isolated from heat-treated blood plasma, the product likewise arises in low yields. This poor efficiency of the isolation of the antithrombin III may be logically explained by a supposition that since the technique of affinity chromatography using heparin relies on the structure in the proximity of the lysine residue, a site for the bondage of antithrombin III to heparin, the structure of this portion is vulnerable to the low-temperature ethanol treatment or the heat treatment. It is, therefore, some other structural site in the antithrombin III that deserves utility for the technique of affinity chromatography. The use of the structure in the proximity of the residue as the center of arginine reaction, therefore, is recommendable. Further, the heparin is not free from virus. The antithrombin III which has been isolated, therefore, has the possibility of being infected with a virus. The circumstances, therefore, have urged the need to search for some other virus-free ligand.

As a measure of the solution of such faults as mentioned above with a view to the points enumerated above, JP-B-59-7,694 and the report of Tomono et al. published in ACTA Haematologica Japonica, Vol. 49, No. 4, 969, 1986 have proposed the use of an inactivated thrombin which, as a virus-free ligand alternative to heparin, reacts with the antithrombin III and exhibits affinity for a covalent bond complex without inducing formation of the complex and, therefore, provides a method for enabling the affinity chromatography utilizing the structure in the proximity of the residue as the center of the arginine reaction of antithrombin III to effect highly efficient fractionation of the antithrombin III contained in the blood plasma and the blood plasma-protein mixture such as of the cold ethanol fraction. Further, the patent specification and the text of the report mentioned above describe examples of the synthesis of anhydrothrombin as an inactivated thrombin from thrombin by the process of synthesis (conventional process A) schematically depicted in FIG. 1. A review of these examples reveals that the reaction for anhydridization requires the reaction system to be adjusted with an alkali to pH 9.0.

The mechanism of the reaction of anhydridization which has been heretofore attained popularly by inactivating the serine residue of such other protein as trypsin or chymotrypsin with a varying sulfonyl fluoride such as phenylmethane sulfonyl fluoride (PMSF) and then treating the inactivated serine residue with an alkali thereby depriving this residue of the PMS (phenylmethane sulfonyl group) modifying the protein is reported in "J. Biochem., 81, 647–656, 1977," "J. Biochem., 81, 657–663, 1977," "Biochemical and Biophysical Research Communications, Vol. 47, No. 6, 1972," and "Biochemical and Biophysical Research Communications, Vol. 46, No. 4, 1972," for example. These reports have statements that in unison purport to demonstrate that the reaction of the anhydridization of the active serine residue in such protein as trypsin or chymotrypsin is allowed to proceed by retaining the modifying protein such as PMSF in a high range of pH (not lower than pH 11). As concerns the anhydridization of thrombin, the aforementioned statement in literature that the reaction proceeds even when the treatment with an alkali is performed in a range of pH (pH 9.0) lower than the range of pH proper for trypsin or chymotrypsin may well deserve attention. Incidentally, the conventional process A taught in the literature mentioned above avoids performing the anhydridization of thrombin in the high range of pH (not lower than pH 11). This avoidance of the high range of pH is logically explained by a supposition that the thrombin cannot be utilized as a ligand because it is not stable in such a high range of pH as fits the trypsin or chymotrypsin and, when subjected at all to the alkali treatment at a pH of not lower than 11, undergoes coagulation and insolubilization and, if permitted to undergo an anhydrodization, will not be enabled to refold it.

Dr. Ashton of the U.S., in his recent report in "Biochemistry 1995, 34, 6454–6463, offers a statement that his replication of the process of synthesis (the conventional process A) which avoids anhydrodizing thrombin in a high range of pH (not lower than pH 11) as disclosed in the literature mentioned above has failed to attain synthesis of the anhydrothrombin, while granting that no simple comparison is allowed because he has used the thrombin originating in bovine blood serum in the place of refined human thrombin ($\alpha$-thrombin originating in Cohn Paste III).

Apart from this assertion, Dr. Ashton describes in the same literature his success in synthesizing the anhydrothrombin owing to the use of guanidine hydrochloride (Gdn-HCl) during the course of reaction indicated in the process of synthesis (conventional process B) schematically illustrated in FIG. 1 for the purpose of precluding the thrombin from coagulation and insolubilization in the high range of pH.

The conventional process B, however, is deficient in practicability because the procedure thereof is complicated, the duration of synthesis thereof is elongated, and the yields in which the anhydrothrombin is produced thereby are extremely low (21% as shown in the data of the literature) as compared with the other processes.

An object of this invention, therefore, is to find a solution of the faults mentioned above and consequently provide a method for the synthesis of an anhydrothrombin which shortens the duration of synthesis, facilitates the procedure, and heightens the yields in which the anhydrothrombin is produced.

The conventional process B shown in FIG. 1 accomplishes the synthesis of an anhydrothrombin by using Gdn- HCl for depriving the thrombin (protein) of hydrophobicity and solubilizing the modified PMS-thrombin. It is suspected that the Gdn-HCl is used for solubilizing the nonpolar residue when the stereostructure of the protein is collapsed by the denaturation due to a change in pH and the nonpolar side chain is consequently exposed to the surface. The addition of the Gdn-HCl which functions as a denaturing agent naturally causes further denaturation of the thrombin and nevertheless brings about successful synthesis of the anhydrothrombin finally by virtue of refolding. The thrombin is unstable as compared with the trypsin and, under the alkaline conditions necessary for the anhydridization, assumes a denatured state which is expressed as $\Delta G$ (denatured free energy)<0. It is believed that the conventional process B uses the Gdn-HCl for the purpose of precluding the occurrence of association and coagulation in this state.

SUMMARY OF THE INVENTION

The present inventors have perfected a method of synthesis which obviates the necessity for adding a denaturing agent intended to minimize the denaturation originating in the alkali treatment used for anhydridization. The thrombin, on exposure to the condition of a high alkali, succumbs to denaturation. At this point, however, it induces no coagulation because of the mutual repulsion of negative charges. Actually, it begins succumbing to coagulation when the pH status is reverted to the neighborhood of neutrality. The synthesis of anhydrothrombin, therefore, is effected by adding glycerin and NaCl for the sake of preventing the coagulation after the alkali treatment and then reverting the pH to the neighborhood of neutrality, and extracting the glycerin subsequently to the refolding. The glycerin, like Gdn-HCl, has a function of precluding the coagulation and, unlike Gdn-HCl, discharges a function of stabilizing a protein. The present invention has been perfected on the basis of the principle which is constructed as described above. It still entrains theoretical points yet to be clarified and may well be regarded as awaiting complete theoretical elucidation. It has been learned, however, that the synthesis of an anhydrothrombin is executed by causing thrombin to react with an inhibitor thereby forming an ester bond with the active serine residue of the thrombin and depriving the thrombin of its activity, and further adding at least one compound selected from the group consisting of alcohols and saccharides (such as, for example, glycerin) and a salt or an amphoteric electrolyte to it by means of an alkali treatment, thereby effecting simultaneously dissociation of the ester bond and exchange of a serine residue for an anhydroalanine residue. It has been further learned that the product is obtained by a simple procedure in high yields (preferably not less than 60%) while attaining necessary refolding without entraining coagulation or association during the existence of a high range of pH or during the reversion of the pH from the high range of the pH mentioned above to the neighborhood of neutrality. The present invention has been perfected on the basis of this knowledge.

Specifically, the object of this invention is accomplished by (1) a method for the synthesis of an anhydrothrombin comprising (A) a step of causing the active serine residue site of thrombin to react with an inhibitor, (B) a step of performing an alkali treatment at a pH of not less than 11, and (C) a step of performing an operation of recovery, and carrying out these steps sequentially in the order mentioned, and characterized by causing at least the step of performing the operation of recovery to proceed in the presence of at least one compound selected from the group consisting of polyhydric alcohols and saccharides, and a salt or an amphoteric electrolyte. The object of this invention is also accomplished by (2) a method according to Item (1) mentioned above, wherein at least one compound selected from the aforementioned group consisting of polyhydric alcohols and saccharides is at least one compound selected from the group consisting of glycerin, ethylene glycol and sucrose.

The object of this invention is also accomplished by (3) a method according to Item (1) or Item (2) mentioned above, wherein
the aforementioned salt or amphoteric electrolyte is at least one compound selected from the group consisting of sodium chloride, potassium chloride, and glycine.

The object of this invention is also accomplished by (4) a method according to any of Items (1)–(3) mentioned above, wherein at least one compound selected from the aforementioned group consisting of polyhydric alcohols and saccharides assumes a proportion of not less than 5% in gravimetric ratio when the compound is liquid or in volumetric ratio when the compound is powder, particles, or solid mass to the whole amount of the relevant reactants under the circumstances of 23° C. of temperature and 50% of relative humidity.

The object of this invention is also accomplished by (5) a method according to any of Items (1)–(4) mentioned above, wherein the concentration of the aforementioned salt or amphoteric electrolyte is not less than 0.2 M.

The method of this invention for the synthesis of an anhydrothrombin comprises a step of causing the active serine residue site of thrombin to react with an inhibitor, a step of performing an alkali treatment at a pH of not less than 11, and a step of performing an operation of recovery and requires these steps to be carried out sequentially in the order mentioned and, owing to the characteristic feature that at least the step of performing the operation of recovery is performed in the presence of at least one compound selected from the group consisting of polyhydric alcohols and saccharides, promotes anhydridization without entraining coagulation and association of a protein during the alkali treatment in a high range of pH, permits necessary refolding to be attained by a simple procedure without inducing coagulation and association during the reversion of pH from the high range of pH to the neighborhood of neutrality in the operation of recovery, and obtains the anhydrothrombin in high yields.

BRIEF DESCRIPTION OF THE DRAWING

FIG. 1 is a simple table schematically illustrating the processes of synthesis (procedures of operation) of anhydrothrombin according to the method of this invention and the conventional method.

DESCRIPTION OF THE PREFERRED EMBODIMENT

Now, this invention will be described more specifically below based on the mode of embodiment thereof.

The method of this invention for the synthesis of an anhydrothrombin comprises

A. a step of causing the active serine residue site of thrombin to react with an inhibitor (first step), B. a step of performing an alkali treatment at a pH of not less than 11 (second step), and C. a step of performing an operation of recovery (third step) and carries out these steps sequentially in the order mentioned, which method is characterized in that at least the step of performing the operation of recovery is performed in the presence of at least one compound selected from the group consisting of polyhydric alcohols and saccharides and a water or an amphoteric electrolyte. To cite an example of this method which uses PMSF specifically as an inhibitor, this method may be expressed by the following reaction formulas (1)

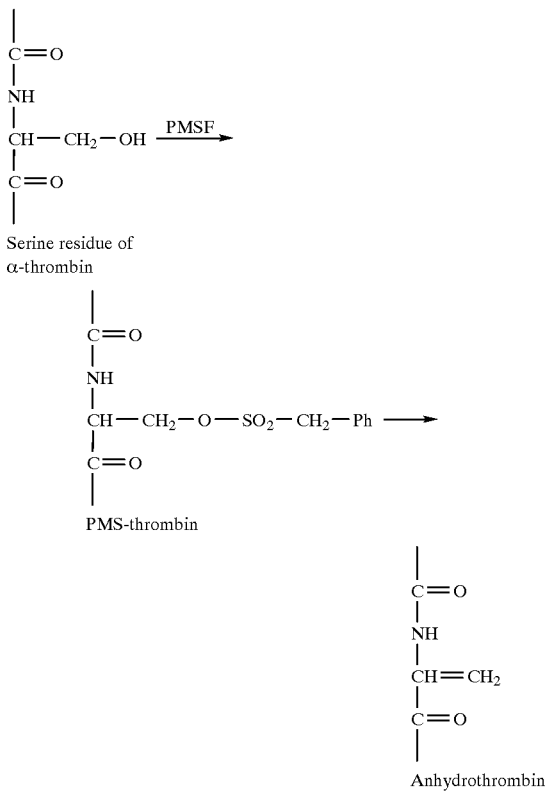

Incidentally, the typical processes of synthesis which pertains to the concrete example under discussion are outlined in FIG. 1.

Now, the method of this invention for the synthesis of anhydrothrombin will be described below by following the first through third step mentioned above.

(A) First step

The first step resides in causing the active serine residue site of thrombin to react with an inhibitor for the purpose of enabling the reaction of thrombin with the inhibitor to form an ester bond between the thrombin and the active serine residue and deprive the thrombin of its activity and can be effected by using the method known to the art. Besides the method taught in the published specification of JP-B-59-7694 or the literature (ACTA Haematologica Japonica, Vol. 45, No. 4, 9696, 1986 or the method taught in the literature (Biochemistry 1995, 34, 6454–6463), for example, the method illustrated in FIG. 1 (method of the present invention) may be adopted.

The thrombin which can be used in the present invention does not need to be particularly limited. Various species of purified thrombin already available in the market such as, for example, the α-thrombin originating in Cohn Paste III, the purified α-thrombin made by Mochida Seiyaku K. K., and the purified α-thrombin made by K. K. Midori Juji can be used in their unmodified form.

The inhibitor which can be used in this invention imposes no particular restriction but requires only to be capable of reacting with the active serine residue of thrombin and forming an ester bond consequently. As concrete examples of the inhibitor answering this description, various species of sulfonyl fluoride such as phenylmethane sulfonyl fluoride (hereinafter referred to occasionally as "PMSF"), 2-phenylethane-1-sulfonyl fluoride, methane sulfonyl fluoride, and p-toluenesulfonyl (tosyl)fluoride and tosyl chloride, diisopropyl fluorophosphoric acid (hereinafter referred to occasionally as "DFP"), 3,4-dichloroisocoumarin (hereinafter referred to occasionally as "3,4-DCI"), L-1-chloro-3-[4-tosyl acid]-7-amino-2-heptanone-hydrochloride (hereinafter referred to occasionally as "TLCK"), and L-1-chloro-3-[4-tosyl acid]-4-phenyl-2-butanone (hereinafter referred to occasionally as "TPCK") may be cited. The inhibitor, prior to the addition thereof to the thrombin, may be prepared in the form of a solution in a solvent such as, for example, methanol, acetone, ethanol, propanol, isopropanol, butanol, propan-2-ol, dimethyl formamide, or dimethyl sulfoxide. The addition of the inhibitor is preferred to be continued until the thrombin activity is confirmed to reach a level of not more than 3%, more advantageously not more than 1%, for the purpose of easing the complication of the subsequent work of separation and removal possibly caused by excessive addition and exalting the reactivity of the added inhibitor as well.

The reaction solvent is only required to comprise a salt solution adding NaCl for the purpose of adjusting the osmotic pressure or equilibrium of ions so as to favor the existence of thrombin or a salt solution adding a composition of several species of ions such as $K^+$, $Ca^{2+}$, and $Mg^{2+}$ and further incorporate therein a buffer system arbitrarily selected from among buffer solutions showing pH values in the range of 2–10, preferably in the range of 4–8, for the sake of stable retention of pH. As concrete examples of the buffer solution answering the description, phosphoric acid buffer solution, carbonate buffer solution, bicarbonate buffer solution, tris buffer solution, citric acid-sodium phosphate buffer solution, succinic acid-sodium hydroxide buffer solution, potassium phthalate-sodium hydroxide buffer solution, imidazole-hydrochloric acid buffer solution, boric acid buffer solution, physiological salt solution, and Good buffer solution may be cited.

As respects the reaction conditions, since a thermal change generally affects seriously the stability of thrombin, the reaction is preferred to be performed at a reaction temperature in the range of (–30)–50° C., preferably in the range of 4–40° C.

The product of the reaction described above is isolated in a refined state by using the method heretofore known to the art. The method to be used for the isolation imposes no particular restriction. As concrete examples of the method usable for the isolation, gel filtration, ion-exchange chromatography, affinity chromatography, ultrafiltration, and dialysis may be cited. To cite a typical gel filtration, the solution resulting from the reaction is added to a column of gel (such as, for example, Sephadex, Biogel, and agarose gel) particles swelled with a solvent and a solvent is continuously passed through the column. This treatment liberates the thrombin product as a high molecular weight solute at first and the inhibitor as a low molecular weight solute later on and consequently effects separation of the two solutes. The solvent which can be used in this treatment is only required to comprise a salt solution adding NaCl for the purpose of adjusting the osmotic pressure or equilibrium of ions so as to favor the existence of thrombin or a salt solution adding a composition of several species of ions such as $K^+$, $Ca^{2+}$, and $Mg^{2+}$ and further incorporate therein a buffer system arbitrarily selected from among buffer solutions showing pH values in the range of 2–10, preferably in the range of 4–8, for the sake of stable retention of pH. As concrete examples of the buffer solution answering the description, phosphoric acid buffer solution, carbonate buffer solution, bicarbonate buffer solution, tris buffer solution, citric acid-sodium phosphate buffer solution, succinic acid-sodium hydroxide buffer solution, potassium phthalate-sodium hydroxide buffer solution, imidazole-hydrochloric acid buffer solution, boric acid buffer solution, physiological salt solution, and Good buffer solution may be cited.

(B) Second step and third step

At the second and the third step, for the purpose of synthesizing an anhydrothrombin by dissociating the ester bond and, at the same time, exchanging the serine residue for a dehydroalanine residue, and further obtaining the anhydrothrombin by a simple procedure in high yields without inducing coagulation or association during the course of refolding by the reversion of pH from the high range of pH to the neighborhood of neutrality, the step of performing an alkali treatment at a pH of not less than 11 (second step) on the thrombin product isolated in a refined state at the first step and the step of performing the operation of recovery of the product are carried out sequentially in the order mentioned. At least the step of performing the operation of recovery is carried out in the presence of at least one compound selected from the group consisting of polyhydric alcohols and saccharides and a salt or an amphoteric electrolyte. This fact characterizes the method of the present invention.

First, the solvent for dissolving the thrombin product isolated in a refined state at the first step is only required to comprise a salt solution adding NaCl for the purpose of adjusting the osmotic pressure or equilibrium of ions so as to favor the existence of thrombin or a salt solution adding a composition of several species of ions such as $K^+$, $Ca^{2+}$, and $Mg^{2+}$ and further incorporate therein a buffer system arbitrarily selected from among buffer solutions showing pH values in the range of 2–10, preferably in the range of 4–8, for the sake of stable retention of pH. As concrete examples of the buffer solution answering the description, phosphoric acid buffer solution, carbonate buffer solution, bicarbonate buffer solution, tris buffer solution, citric acid-sodium phosphate buffer solution, succinic acid-sodium hydroxide buffer solution, potassium phthalate-sodium hydroxide buffer solution, imidazole-hydrochloric acid buffer solution, boric acid buffer solution, physiological salt solution, and Good buffer solution may be cited.

At least one compound selected from the group consisting of polyhydric alcohols and saccharides and used in combination with a salt or an amphoteric electrolyte in this invention is intended to promote the anhydridization of thrombin without inducing coagulation and association of a protein in the alkali treatment performed in the high range of pH and effect the refolding of the anhydrothrombin without inducing coagulation and association in the operation of recovery during the reversion of pH from the high range of pH to the neighborhood of neutrality. The object of this invention can be accomplished even by using the operation of recovery alone.

As concrete examples of at least one compound selected from the aforementioned group consisting of polyhydric alcohols and saccharides, polyhydric alcohols (inclusive of sugar alcohols) such as tetrytols (typically represented by erythritol, D-threitol, L-threitol, and D,L-threitol), pentitols (typically represented by ribitol, D-arabinitol, L-arabinitol, D,L-arabinitol, and xylitol), hexitols (typically represented by allitol, dulcitol (galactitol), sorbitol (D-glucitol), L-glucitol, D,L-glucitol, D-mannitol, L-mannitol, D,L-mannitol, D-altritol, L-altritol, D,L-altritol, D-iditol, and L-iditol), heptitol, maltitol, lactitol, glycerin, ethylene glycol, diethylene glycol, triethylene glycol, propylene glycol, dipropylene glycol, 1,3-butylene glycol, neopentyl glycol, pentamethylene glycol, hexamethylene glycol, pentaerythritol, dipentaerythritol, tripentaerythritol, trimethylol ethane, trimethylol propane, ennaheptitol anhydride, 1,4-butane diol, 1,2,4-butane triol, and 1,2,6-hexane triol and saccharides such as glycerin aldehyde dioxy-acetone, threose, erythrulose, erythrose, arabinose, ribulose, ribose, xylose, xylulose, lyxose, glucose, fructose, mannose, idose, sorbose, gulose, talose, tagatose, galactose, allose, psicose, altrose, and sucrose may be cited. These compounds may be used either singly or in the form of a mixture of two or more members. Among other compounds mentioned above, at least one compound selected from the group consisting of glycerin, ethylene glycol, and sucrose proves to be particularly preferable.

At least one compound selected from the aforementioned group consisting of polyhydric alcohols and saccharides is preferred to assume a proportion of not less than 5%, favorably not less than 15%, in gravimetric ratio when the compound is liquid or in volumetric ratio when the compound is powder, particles, or solid mass to the whole amount of the relevant reactants under the circumstances of 23° C. of temperature and 50% of relative humidity. Even when this proportion to the whole is less than 5%, the second and the third step can be effectively performed to attain the effect aimed at by relatively heightening the concentration of the salt or amphoteric electrolyte to be used in combination with the one compound mentioned above. The proportion (concentration) of the one compound selected from the aforementioned group consisting of polyhydric alcohols and saccharides, therefore, is preferred to be suitably decided at a level, depending on the kind of compound, so as to manifest advantageously the effect aimed at. In making this decision, consideration must be given to the kind and concentration of the salt or amphoteric electrolyte to be used in combination with the one compound.

The salt or amphoteric electrolyte to be used in combination with at least one compound selected from the group consisting of polyhydric alcohols and saccharides in this invention is intended to promote the anhydridization of thrombin without inducing coagulation and association of a protein in the alkali treatment performed in the high range of pH and effect the refolding of the anhydrothrombin without inducing coagulation and association in the operation of recovery during the reversion of pH from the high range of pH to the neighborhood of neutrality. It imposes no particular restriction but requires only to obtain such salt concentration (ion intensity) and dielectric constant as fit the object just mentioned. The choice between organicity and inorganicity is irrelevant for the salt or amphoteric electrolyte.

As concrete examples of the salt or amphoteric electrolyte mentioned above, halogenated alkali metals such as sodium chloride and potassium chloride, halogenated alkaline earth metals such as magnesium chloride and calcium chloride, inorganic acid salts such as ammonium chloride, ammonium sulfate, sodium carbonate, potassium carbonate, magnesium carbonate, ammonium carbonate, calcium carbonate, sodium hydrogen carbonate, calcium hydrogen carbonate, potassium hydrogen carbonate, ammonium hydrogen carbonate, sodium phosphate, disodium hydrogen phosphate, potassium dihydrogen phosphate, diammonium hydrogen phosphate, sodium borate, and potassium borate, organic acid salts such as sodium citrate, potassium citrate, magnesium citrate, calcium citrate, ammonium citrate, sodium phthalate, potassium phthalate, magnesium phthalate, calcium phthalate, ammonium phthalate, sodium succinate, potassium succinate, magnesium succinate, calcium succinate, ammonium succinate, sodium acetate, potassium acetate, calcium acetate, magnesium acetate, and ammonium acetate, and such salts or amphoteric electrolytes as amines which are fated to convert into such amphoteric electrolytes as glycin and alanine may be cited. These salts or amphoteric electrolytes may be used either singly or in the form of a mixture of two or more members. Among other compounds mentioned above, such low molecular alkali metal salts, inorganic salts, and amphoteric electrolytes as allow ready solution in water, permit easy adjustment of the ion intensity (salt concentration) and dielectric constant optimum for the concentration of the at least one compound selected from the aforementioned group consisting of polyhydric alcohols and saccharides to be used in combination therewith prove to be particularly advantageous. Specifically, it may well be concluded that at least one compound selected from the group consisting of sodium chloride, potassium chloride, and glycin is advantageously used.

The concentration of the salt or amphoteric electrolyte mentioned above advantageously is not less than 0.2 M, preferably not less than 0.5 M. Even when this concentration is less than 0.2 M, the second and the third step can be effectively carried out and the effect aimed at can be satisfactorily manifested by relatively heightening the proportion of this compound to the whole reactants, similarly to the at least one compound selected from the aforementioned group consisting of polyhydric alcohols and saccharides.

At the second step, for the treatment with an alkali to effect the anhydridization as required, the alkali is added to the reaction system to adjust the pH of the reaction system to a level of not less than 11 (when necessary, in the presence of at least one compound selected from the aforementioned group consisting of polyhydric alcohols and saccharides in conjunction with a salt or an amphoteric electrolyte) and the reaction temperature is maintained at a level in the range of (−30)–50° C., preferably 4–40° C. If the pH value is less than 11, the shortage will bring about the disadvantage of precluding the PMSF-removing reaction from arising and preventing the anhydridization from proceeding. As concrete examples of the alkali mentioned above, univalent bases such as sodium hydroxide and potassium hydroxide, bivalent bases such as calcium hydroxide, barium hydroxide, calcium oxide, magnesium oxide, calcium carbonate, and sodium carbonate, and trivalent bases such as iron hydroxide may be cited. If the reaction temperature is less than −30° C., the reaction system will suffer the disadvantage of being possibly frozen. Conversely, if this temperature exceeds 50° C., the reaction system will incur the disadvantage that the thrombin succumbs to denaturation of protein and no longer resumes the original state in spite of a subsequent work of refolding.

(C) Third step

Then, at the third step, the solution containing the anhydrothrombin synthesized by the alkali treatment mentioned above is subsequently (after the reaction of anhydridization) caused to resume the original state (stereostructure) by the work of refolding which is performed in the presence of at least one compound selected from the aforementioned group consisting of polyhydric alcohols and saccharides in conjunction with a salt or an amphoteric electrolyte. The work of refolding mentioned above does not impose any particular restriction but may employ the method heretofore known to the art. For example, a method which comprises adjusting the pH of the system (solution) resulting from the reaction to a level in the range of 4–10 with a solvent (the same solvent as used in the reaction of anhydridization mentioned above) and then retaining the treated system at a temperature in the range of (−30)–50° C. for a fixed duration or a method which comprises adjusting the pH to a level in the range of 4–10 by means of dialysis may be employed.

Subsequently, the anhydrothrombin which has undergone the work of refolding is subjected to purification and separation for the purpose of removing the at least one compound selected from the group consisting of polyhydric alcohols and saccharides and allowed to continue its presence in the reaction system and further removing the salt or amphoteric electrolyte required to be removed (the elaborate separation and removal may be omitted where the extracting solution to be used for the final extraction of the anhydrothrombin tolerates the presence of such a salt as NaCl or phosphoric acid salt or an amphoteric electrolyte). The method for the purification and separation does not impose any particular restriction but may employ the procedure heretofore known to the art. As concrete examples of the method which fits the purification and separation, dialysis, ultrafiltration, gel chromatography, ion-exchange chromatography, and affinity chroma-tography may be cited. In the typical operation of dialysis, the at least one compound selected from the group consisting of polyhydric alcohols and saccharides is dialyzed from the refolded anhydrothrombin solution through a membrane of cellulose, for example, into a solvent(the same solvent as used in the reaction of anhydridization mentioned above or in the work of refolding) having a pH in the range of 4–10.

Then, the operation of purification and separation is carried out for the purpose of removing an impurity and obtaining the anhydrothrombin aimed at. The method for the purification and separation does not impose any particular restriction but may employ the procedure for purification and separation heretofore known to the art. For example, a method which, as schematically depicted in FIGURE 1, comprises concentrating as with a YM-10 membrane the anhydrothrombin solution removed the at least one compound selected from the group consisting of polyhydric alcohols and saccharides, then cleaning the concentrated solution by passage through a column of benzamidine cepharose equilibrated with a solvent (the same solvent as used in the reaction of anhydridization mentioned above or the work of refolding) having a pH in the range of 4–10, eluting the adsorbate from the column with a benzamidine solution (which may contain such a salt as sodium chloride, potassium chloride, calcium chloride, or magnesium chloride for the purpose of causing specific adsorption of the protein aimed at) having a pH adjusted in the range of 4–10, and dialyzing the eluate with a solvent(the same solvent as used in the reaction for the anhydridization mentioned above or the work of refolding) having a pH in the range of 4–10 for the purpose of removing the benzamidine and effecting the extraction of the anhydrothrombin aimed at, or a method which resorts to separation by ultrafiltration or gel filtration with a column of Sephadex may be cited.

Now, this invention will be specifically described below with reference to working examples.

EXAMPLE 1

(1) Synthesis of PMS-thrombin

To a solution having 10.0 mg of thrombin originating in bovine blood dissolved in a 5 mM phosphoric acid buffer containing 0.1 M NaCl solution of pH 6.5, 30 μl of a 7% phenyl methane sulfonyl fluoride (PMSF) methanol solution was added at intervals of 30 minutes until the total activity reached less than 1%. The resultant solution was subjected to gel filtration with the same buffer.

(2) Anhydridization of PMS-thrombin

The PMS-thrombin was adjusted with the buffer mentioned above to a total volume of 20 ml and cooled to 0° C. 1.05 ml of 1 M NaOH added thereto (with the pH raised consequently to about 12.5) were left reacting at 0° C. for 12 minutes. To the resultant reaction mixture, 10 ml of 3 M NaCl was added and glycerin was further added in an amount calculated to give a final concentration of 50 vol %. The produced mixture was adjusted to pH 8 by the addition of 1 M Tris —HCl of pH 7. The resultant solution was left standing at 4° C. for 12 hours, then dialyzed against a 50 mM Tris-HCl containing 1 M NaCl solution of pH 7.5, and again dialyzed against a 50 mM Tris-HCl containing 0.1 M NaCl solution of pH 7.5.

(3) Separation of anhydrothrombin through a column of benzamidine cepharose

The anhydrothrombin solution which the glycerin had been removed was concentrated to a volume of about 20 ml by the use of a YM-10 membrane and added to a column of benzamidine cepharose equilibrated with a 50 mM Tris-HCl buffer containing 0.1 M NaCl solution of pH 7.5. The column was washed with the same solution until an impurity peak ceased to occur and the anhydrothrombin adsorbed on the column was extracted with a 50 mM Tris-HCl buffer containing 0.1 M NaCl and a 0.2 M benzamidine solution of pH 7.5. The extracted solution was dialyzed against a 50 mM Tris-HCl buffer containing 1 M NaCl solution of pH 6.5 to effect removal of the benzamidine. The extracted anhydrothrombin solution contained 7.3 mg of protein and exhibited thrombin activity of 0.7%. The yield was 73%.

EXAMPLE 2

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while using KCl in place of the NaCl added and used for dialysis in the anhydridization of PMS-thrombin at the step (2). The anhydrothrombin solution obtained by the extraction contained 6.0 mg of protein and exhibited a thrombin activity of 0.5% as shown in Table 1. The yield was 60%.

EXAMPLE 3

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while using glycine in place of the NaCl added and used for dialysis in the anhydridi-zation of PMS-thrombin at the step (2). The anhydrothrombin solution obtained by the extraction contained 5.5 mg of protein and exhibited a thrombin activity of 0.5% as shown in Table 1. The yield was 55%.

EXAMPLE 4

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while using ethylene glycol in place of the glycerin added for the anhydridization of PMS-thrombin at the step (2). The anhydrothrombin solution obtained by the extraction contained 7.0 mg of protein and exhibited a thrombin activity of 0.5% as shown in Table 1. The yield was 70%.

EXAMPLE 5

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while using thrombin originating in human blood instead as the starting protein. The anhydrothrombin solution obtained by the extraction contained 6.9 mg of protein and exhibited a thrombin activity of 0.5% as shown in Table 1. The yield was 69%.

EXAMPLE 6

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while changing the amount of NaOH used for alkali addition in the anhydridization of PMS-thrombin at the step (2) from 1.05 ml to 0.8 ml, changing the reaction time from 12 minutes to 15 minutes, and changing the glycerin concentration from 50 vol. % to 30 vol %. The anhydrothrombin solution obtained by the extraction contained 6.0 mg of protein and exhibited a thrombin activity of 0.3% as shown in Table 1. The yield was 60%.

EXAMPLE 7

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while using 30 wt. % of sucrose in lace of the glycerin added in the anhydridization of PMS-thrombin at the step (2). The anhydrothrombin solution obtained by the extraction contained 6.0 mg of protein and exhibited a thrombin activity of 0.4% as shown in Table 1. The yield was 60%.

EXAMPLE 8

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while changing the glycerin concentration in the anhydridization of PMS-thrombin at the step (2) from 50 vol. % to 8 vol %. The anhydrothrombin solution obtained by the extraction contained 2.0 mg of protein and exhibited a thrombin activity of 0.3% as shown in Table 1. The yield was 20%.

EXAMPLE 9

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while changing the amount of the 3 M NaCl added and used for dialysis in the anhydridi-zation of PMS-thrombin at the step (2) from 10 ml to such an amount as to give a final concentration of 0.2 M NaCl. The anhydrothrombin solution obtained by the extraction contained 2.5 mg of protein and exhibited a thrombin activity of 0.6% as shown in Table 1. The yield was about 25%.

EXAMPLE 10

An anhydrothrombin wished to be obtained was extracted by sequentially performing the steps of (1) synthesis of PMS-thrombin, (2) anhydridization of PMS-thrombin, and (3) separation of anhydrothrombin through a column of benzamidine cepharose by following the procedure of Example 1 while using NaOH for adjusting a pH to 11.5 instead of adding NaOH in the amount of 1.05 ml and changing the reaction time from 12 minutes to 6 hours in the anhydridization of PMS-thrombin at the step (2). The anhydrothrombin solution obtained by the extraction contained 6.0 mg of protein and exhibited a thrombin activity of 0.4% as shown in Table 1. The yield was about 60%.

Control 1

The steps of (1) synthesis of PMS-thrombin and (2) anhydrid-ization of PMS-thrombin were sequentially performed by following the procedure of Example 1 while changing the glycerin concentra-tion in the anhydridization of PMS-thrombin at the step (2) from 50 vol. % to 3 vol %. During the operation of recovery by the reversion of pH to the neighborhood of neutrality after the alkali treatment, however, the reaction solution developed coagulation and the protein was consequently insolubilized and precipitated and the operation could no longer be continued. Since the precipitated insolubilized protein could not be tested for thrombin activity, the thrombin activity was measured at the stage of PMS-thrombin. The result was 0.7%.

Control 2

The steps of (1) synthesis of PMS-thrombin and (2) anhydrid-ization of PMS-thrombin were sequentially performed by following the procedure of Example 1 while the addition of NaCl was omitted and the dialysis was performed with a solution containing no NaCl in the anhydridization of PMS-thrombin at the step (2). During the operation of recovery by the reversion of pH to the neighbor-hood of neutrality after the alkali treatment, however, the reaction solution developed coagulation and the protein was consequently insolubilized and precipitated and the operation could no longer be continued. Since the precipitated insolubilized protein could not be tested for thrombin activity, the thrombin activity was measured at the stage of PMS-thrombin. The result was 0.5%.

Control 3

The steps of (1) synthesis of PMS-thrombin, (2) anhydridi-zation of PMS-thrombin, and (3) separation of anhydrothrombin through a column of benzamidine cepharose were sequentially performed by following the procedure of Example 1 while using NaOH for adjusting a pH to 10 instead of adding NaOH in an amount of 1.05 ml and changing the reaction time from 12 minutes to 48 hours in the anhydridization of PMS-thrombin at the step (2). The extracted solution contained a protein in an unmeasurably small amount and the presence of protein therein could not be confirmed even by electrophoresis of SDS-PAGE. The impurity peak of the effluent from the column of benzamidine cepharose was very large. The relevant fraction of the effluent was found to contain 9.3 mg of protein. The results imply that the thrombin anhydridized by the method described above was not adsorbed on the column of benzamidine cepharose and that the greater part thereof leaked from the column. The leakage may be interpreted as resulting from the failure of the PMS-thrombin to undergo anhydridization.

TABLE 1

| | Kind of thrombin | Kind of Poly-hydric alcohol/saccha-ride | Concent-ration of polyhydric alcohol/Saccharide (vol or wt %) | Kind of salt/amphoteric electro-lyte | Concent-ration of salt/amphoteric electro-lyte | pH | Duration of anhydridization | Thrombin activity (%) | Final amount of an-hydro-thrombin in (mg) | Yield of anhyd ro-thromb bin (%) |
|---|---|---|---|---|---|---|---|---|---|---|
| Example 1 | originating in bovine blood | Glycerin | 50 | NaCl | 1M | 12.5 | 12 min | 0.7 | 7.3 | 73 |
| Example 2 | originatingin bovine blood | Glycerin | 50 | KCl | 1M | 12.5 | 12 min | 0.5 | 6.0 | 60 |
| Example 3 | originating in bovine blood | Glycerin | 50 | glycin | 1M | 12.5 | 12 min | 0.5 | 5.5 | 55 |
| Example 4 | originating in bovine blood | Ethylene glycol | 50 | NaCl | 1M | 12.5 | 12 min | 0.5 | 7.0 | 70 |
| Example 5 | originating in bovine blood | Glycerin | 50 | NaCl | 1M | 12.5 | 12 min | 0.5 | 6.9 | 69 |
| Example 6 | originating in bovine blood | Glycerin | 30 | NaCl | 1M | 12.5 | 15 min | 0.3 | 6.0 | 60 |
| Example 7 | originating in bovine blood | Sucrose | 30 | NaCl | 1M | 12.5 | 12 min | 0.4 | 6.0 | 60 |
| Example 8 | originating in bovine blood | Glycerin | 8 | NaCl | 1M | 12.5 | 12 min | 0.3 | 2.0 | 20 |

TABLE 1-continued

| | Kind of thrombin | Kind of Polyhydric alcohol/saccharide | Concentration of polyhydric alcohol/Saccharide (vol or wt %) | Kind of salt/amphoteric electrolyte | Concentration of salt/amphoteric electrolyte | pH | Duration of anhydridization | Thrombin activity (%) | Final amount of anhydrothrombin (mg) | Yield of anhydrothrombin (%) |
|---|---|---|---|---|---|---|---|---|---|---|
| Example 9 | originating in bovine blood | Glycerin | 50 | NaCl | 0.2M | 12.5 | 12 min | 0.6 | 2.5 | 25 |
| Example 10 | originating in bovine blood | Glycerin | 50 | NaCl | 1M | 11.5 | 6 hours | 0.4 | 6.0 | 60 |
| Control 1 | originating in bovine blood | Glycerin | 3 | NaCl | 1M | 12.5 | 12 min | 0.7 | Protein (anhydrothrombin) | |
| Control 2 | originating in bovine blood | Glycerin | 50 | None | — | 12.5 | 12 min | 0.5 | insolubilized and precipitated | |
| Control 3 | originating in bovine blood | Glycerin | 50 | NaCl | 1M | 10 | 48 hours | — | No anhydridization attained | |

Control 4

(1) Synthesis of PMS-thrombin

In 1 ml of a 50 mM Tris-hydrochloric acid buffer solution (pH 8.0) containing 0.1 M NaCl, 35 mg of α-thrombin originating in Cohn Paste III was dissolved at rate of 0.3 mg per ml. The produced solution was kept at 20° C. for five minutes. To this solution, PMSF (300 mM methanol solution) was added to prepare a solution of 3 mM in concentration. This solution was kept warm for two hours. The thrombin activity of the resultant solution was not higher than 0.1%.

(2) Anhydridization of PMS-thrombin

The solution from the step (1) was adjusted to pH 9.0 with 0.1 N NaOH and was dialyzed against a 50 mM Tris-hydrochloric acid buffer solution containing 0.1 M NaCl for 24 hours.

(3) Separation of anhydrothrombin through a column of benzamidine cepharose

The dialyzed solution from the step (2) was concentrated by the use of an Amicon ultrafiltration membrane system fitted with a PM 10 membrane and then adjusted to pH 7.5 with 0.1 N HCl. The resultant solution was passed through a column of benzamidine cepharose equilibrated with a 50 mM Tris-hydrochloric acid buffer solution (pH 7.5) containing 0.1 M NaCl and washed with the same buffer solution until perfect elution of a leak peak. The peak which leaked at this time was found by a test to contain 31 mg of protein. When it was tested for molecular weight by the SDS-PAGE electrophoresis, the result was about 39,500. This molecular weight is substantially equal to that of the α-thrombin originating in Cohn Paste III. The adsorbate in the column was eluted by passing a stream of 0.2 M benzamidine (pH 7.5) through the column and was dialyzed with a 50 mM Tris-hydrochloric acid buffer solution containing 0.1 M NaCl for 24 hours to effect removal of benzamidine. This solution contained a protein in an unmeasurably small amount and the presence of protein therein could not be confirmed even by electrophoresis of SDS-PAGE. The impurity peak of the effluent from the column of benzamidine cepharose was very large. The relevant fraction of the effluent was found to contain 30.2 mg of protein. The results imply that the thrombin anhydridized by the method described above was not adsorben the column of benzamidine cepharose and that the greater part thereof leaked from the column. The leakage may be interpreted as resulting from the failure of the PMS-thrombin to undergo anhydridization. The solution was analyzed for a dehydroalanine for the precautions' sake. The data of the analysis are shown in Table 2 given below. The dehydroalanine serves as an index of anhydridization; an increase of the numerical value of dehydroalanine implies liberation of PMSF from the PMS-thrombin and consequent anhydridization. The analysis failed to detect any increase of the dehydroalanine concentration. The data plus the results mentioned above justify a conclusion that no anhydridization of thrombin occurred herein.

TABLE 2

| | | 30 min | 24 hr | Adsorption on column |
|---|---|---|---|---|
| Solution of PMS-thrombin at step (2) | First round | | 71 nmol | No adsorption |
| | Second round | | 91 nmol | No adsorption |
| Solution at step (3) after 24 hours' treatment at pH 9 | First round | 94 nmol | 106 nmol | No adsorption |
| | Second round | | 81 nmol | No adsorption |
| Thrombin treated with 0.1 N NaOH | | 329 nmol | | No adsorption |

The thrombin samples used in the test were prepared by separating parts of the products obtained by synthesis at the relevant steps and adjusting them to a prescribed concentration.

Control 5

(1) Synthesis of PMS-thrombin

In 10 ml of a 50 mM phosphoric acid buffer solution (pH 6.5) containing 0.15 M NaCl and 0.1% PEG, 24 mg of thrombin originating in bovine blood plasma was dissolved. To this solution, 26 μl of a 7% PMSF methanol solution was added three times at intervals of 30 minutes. The solution was maintained at room temperature during the course of reaction. After this reaction, the solution exhibited a thrombin activity of not more than 1%. The PMS-thrombin solution was injected into a column of Sephadex G-25 equilibrated with a 10 mm phosphoric acid buffer solution (pH 6.5) containing 0.1 M NaCl and 0.1% PEG to effect exchange of buffer solutions. The sample consequently obtained was concentrated to 2.4 ml by the use of an Amicon ultrafiltra-tion membrane system fitted with a YM-10 membrane.

(2) Anhydridization of PMS-thrombin

In 12 ml of 6N Gdn-HCl (0° C.), 120 μl of 6N NaOH added thereto was rapidly stirred. This solution was anhydridized by the addition of 2.4 ml (0° C.) of the PMS-thrombin mentioned above. This reaction was continued as stirred for 10 minutes and then stopped by the addition of 15 ml (0° C.) of a 0.4 M phosphoric acid buffer solution (pH 6). The solution, 29.4 ml in volume, which resulted from the reaction was added dropwise to 300 ml of a phosphoric acid buffer solution containing 0.75 M NaCl and 0.1% PEG. After the dropwise addition, the produced solution was concentrated to 10 ml by the use of an Amicon ultrafiltration membrane system fitted with a YM-10 membrane. To the resultant concentrated solution, 20 hours after the dropwise addition mentioned above, 26 μl of a 7% PMSF methanol solution was added at intervals of 30 minutes until the thrombin activity reached to less than 1%.

(3) Separation of anhydrothrombin through a column of benzamidine cepharose

The anhydrothrombin from the step (2) was injected into a column of Sephadex G-25 equilibrated at pH 6.5 with a 25 mM phosphoric acid buffer solution containing 0.1 M NaCl and 0.1% PEG to effect exchange of buffer solutions. The resultant solution was further added to a column of benzamidine cepharose equilibrated at pH 6.5 with a 5 mM phosphoric acid buffer solution containing 0.1% PEG. It was washed with the same buffer solution until the peak ceased to appear. The adsorbate in the column was eluted with 0.2 M benzamidine (pH 6.5) containing 0.1 M NaCl and the eluate was obtained in three fractions of 20 ml (60 ml in total). The fractions of the solution were analyzed for protein content to confirm the fraction containing the anhydrothrombin. This fraction was dialyzed against a 50 mM phosphoric acid buffer solution (pH 6.5) containing 0.1 M NaCl to effect removal of benzamidine. The solution was found to contain 7.1 mg of protein (yield 30%).

This method synthesized the anhydrothrombin in a yield of 30%.

The entire disclosure of Japanese Patent Application No.9-148,116 filed on Jun. 5, 1997, and Japanese Patent Application No.10-120,859 filed on Apr. 30, 1998 including specification, claims, drawing and summary are incorporated herein by reference in its entirety.

What is claimed is:

1. A method for the synthesis of an anhydrothrombin comprising (A) reacting an active serine residue site of thrombin with an inhibitor, (B) subjecting the thrombin resulting from step (A) to an alkali treatment at a pH of not less than 11, (C) recovering the anhydrothrombin resulting from step (B) wherein said recovery occurs in the presence of at least one compound selected from the group consisting of polyhydric alcohols and saccharides, and a salt or an amphoteric electrolyte.

2. A method according to claim 1, wherein said at least one compound selected from the group consisting of polyhydric alcohols and saccharides is at least one compound selected from the group consisting of glycerin, ethylene glycol, and sucrose.

3. A method according to claim 1, wherein said salt or amphoteric electrolyte is at least one compound selected from the group consisting of sodium chloride, potassium chloride, and glycine.

4. A method according to claim 2, wherein said salt or amphoteric electrolyte is at least one compound selected from the group consisting of sodium chloride, potassium chloride, and glycine.

5. A method according to claim 1, wherein said at least one compound selected from the group consisting of polyhydric alcohols and saccharides assumes a proportion of not less than 5% in gravimetric ratio when the compound is liquid or in volumetric ratio when the compound is powder, particles, or solid mass to the whole amount of the relevant reactants under the circumstances of 23° C. of temperature and 50% of relative humidity.

* * * * *